(12) United States Patent
Wilson et al.

(10) Patent No.: US 12,370,364 B1
(45) Date of Patent: Jul. 29, 2025

(54) MICROCURRENT STIMULATION SYSTEMS, METHODS, AND DEVICES FOR TREATMENT OF VISUAL IMPAIRMENTS

(71) Applicant: B-21, LLC, Dover, DE (US)

(72) Inventors: David D. Wilson, Siloam Springs, AR (US); Melinda K. Wilson, Siloam Springs, AR (US); James Schmied, Pollock Pines, CA (US); John Sellers, Placerville, CA (US)

(73) Assignee: B-21, LLC, Bentonville, AR (US)

( * ) Notice: Subject to any disclaimer, the term of this patent is extended or adjusted under 35 U.S.C. 154(b) by 0 days.

(21) Appl. No.: 18/947,825

(22) Filed: Nov. 14, 2024

Related U.S. Application Data

(60) Provisional application No. 63/702,284, filed on Oct. 2, 2024.

(51) Int. Cl.
  *A61N 1/36* (2006.01)
  *A61N 1/04* (2006.01)

(52) U.S. Cl.
  CPC ....... *A61N 1/36046* (2013.01); *A61N 1/0464* (2013.01); *A61N 1/0472* (2013.01); *A61N 1/3603* (2017.08)

(58) Field of Classification Search
  CPC .............. A61N 1/36046; A61N 1/0464; A61N 1/0472; A61N 1/3603
  See application file for complete search history.

(56) References Cited

U.S. PATENT DOCUMENTS

| | | |
|---|---|---|
| 5,522,864 A | 6/1996 | Wallace et al. |
| 6,035,236 A | 3/2000 | Jarding et al. |
| 7,877,148 B2 | 1/2011 | Chowdhury et al. |
| 9,220,894 B1 | 12/2015 | Zhu |
| 10,456,579 B2 | 10/2019 | Salazar |
| 11,007,367 B2 | 5/2021 | O'Clock |
| 11,116,973 B1 | 9/2021 | Masko et al. |
| 11,351,374 B2 | 6/2022 | Mowery et al. |
| 11,865,340 B2 | 1/2024 | Masko |

(Continued)

FOREIGN PATENT DOCUMENTS

WO  2021177968 A1  9/2021

*Primary Examiner* — Ankit D Tejani
*Assistant Examiner* — Joshua Brendon Solomon
(74) *Attorney, Agent, or Firm* — Quinn IP Law

(57) ABSTRACT

Presented are electrical microcurrent systems for treating ocular diseases, methods for making/using such microcurrent systems, and wearable microcurrent devices for treatment of macular degeneration. A microcurrent system for treating an ocular disease includes a mounting support, e.g., that mounts inside a housing shell of a microcurrent headset unit. Mounted onto the mounting support, e.g., inside the housing shell, are a power source that stores and dispenses electrical power, and a system controller that electrically connects to and controls the electrical output of the power source. A pair of electrically conductive eyecups is attached to the mounting support and electrically connected to the power source to receive therefrom an electrical microcurrent. Each eyecup may be a single-piece structure that includes a pair of terminal rails projecting from respective sides of a longitudinal end of an elongated pedestal. The terminal rails are shaped and sized to contact an eyelid of a user.

20 Claims, 4 Drawing Sheets

(56) References Cited

U.S. PATENT DOCUMENTS

| | | | |
|---|---|---|---|
| 2014/0327871 A1* | 11/2014 | Hall | G02C 11/08 |
| | | | 351/158 |
| 2017/0266446 A1 | 9/2017 | O'Clock | |
| 2018/0318586 A1* | 11/2018 | Salazar | A61N 1/36046 |
| 2020/0171307 A1* | 6/2020 | Rockley | G02C 5/001 |
| 2023/0181028 A1 | 6/2023 | Duncan et al. | |

* cited by examiner

MICROCURRENT STIMULATION SYSTEMS, METHODS, AND DEVICES FOR TREATMENT OF VISUAL IMPAIRMENTS

CLAIM OF PRIORITY AND CROSS-REFERENCE TO RELATED APPLICATION

This application claims the benefit of and priority to U.S. Provisional Patent Application No. 63/702,284, which was filed on Oct. 2, 2024, and is incorporated herein by reference in its entirety and for all purposes.

TECHNICAL FIELD

The present disclosure relates generally medical devices and procedures for treating visual impairments. More specifically, aspects of this disclosure relate to electrical microcurrent stimulation devices for treating age-related macular degeneration (AMD).

INTRODUCTION

Impairment and loss of vision can result from a myriad of etiologies, including ocular diseases that cause deterioration of the retina, such as age-related macular degeneration, Stargardt macular dystrophy, retinitis pigmentosa, and other medical conditions. Macular degeneration—or AMD—is an eye disease that damages the macula lutea in the rear of the oculus opposite the lens, the part of the eye which is responsible for seeing details at the center of the field of vision. AMD is a common eye health problem that affects an estimated 20 million people in the United States alone and is the leading cause of permanent close-up (reading) vision impairment in people 65 and older. There are two common types of AMD: (1) exudative "wet" macular degeneration, which is caused by abnormal blood vessels leaking proteins and lipids into the eye; and (2) atrophic "dry" macular degeneration, which is caused by the gradual thinning of the macula. A common treatment for AMD that has been shown to successfully ameliorate the ophthalmoscopic manifestations of the disorder while restoring central visual acuity to visually impaired patients is electrical stimulation of the eye and optic nerve with extraocular electrodes. Application of an electrical microcurrent to the eye has proven to both heal cells and tissues that were damaged by AMD and to activate surviving nervous cells in the eye that lost their natural input due to the degenerative effects of the disease.

SUMMARY

Presented below are electrical microcurrent systems for treating ocular diseases, methods for making and methods for using any of the herein described microcurrent systems and devices, and wearable microcurrent devices for treatment of ocular diseases. In a non-limiting example, a standalone microcurrent headset unit contains a pair of electrically conductive eyecups that are structurally engineered to contact the palpebra cutanea of the user's upper and lower eyelid flaps to transmit therethrough a therapeutic microcurrent, e.g., of about 20 to about 500 microamps (µA). This design eliminates the use of electrodes that are placed directly against the scleral surfaces of the eyes or on the orbicularis oculi region or cranium of the user's head, which are less efficient and oftentimes painful. To accommodate users of varying cranial girth and facial topographies, each eyecup may be adjustable in both an antero-posterior direction, i.e., along the sagittal plane, and a medio-lateral direction, i.e., along the coronal plane. The standalone unit is also sufficiently small (e.g., a handheld device weighing less than 5-7 lbs) and comes originally equipped with an onboard power source and a user interface that enables the user to operate the device without assistance or the need of an external computer or a bulky battery pack.

Aspects of this disclosure are directed to therapeutic microcurrent systems for treating ocular diseases, such as retinal disorders and other visual impairments. In an example, there is presented a microcurrent system for treating an ocular disease of a user. The microcurrent system includes a mounting support, e.g., that mounts onto a countertop ophthalmic kiosk or inside a microcurrent headset unit. The microcurrent system also includes a power source, which stores and dispenses electrical power, and a system controller, which electrically connects to and controls the electrical input/output of the power source. Both the power source and system controller may be removably attached, either directly or indirectly, to the mounting support. A pair of electrically conductive eyecups is attached to the mounting support and electrically connected to the power source to receive therefrom an electrical microcurrent. Each eyecup includes an elongated and rigid pedestal with a pair of arched terminal rails that each projects from a respective side of a longitudinal (posterior) end of the pedestal. The terminal rails of each eyecup are structurally configured (e.g., shaped, sized, and oriented) to contact a respective eyelid of the user, e.g., to transmit an electrical microcurrent to the user's eyes.

Additional aspects of this disclosure are directed to wearable microcurrent devices for treatment of ocular disorders and impartments. In an example, there is presented a microcurrent headset unit for treating an ocular disease of a user. The microcurrent headset unit includes a headgear component that is structurally configured to be worn on the user's head. The headgear component includes a face goggle, e.g., with a face pad, that presses against the user's face, and a housing shell that is removably mounted onto an anterior side the face goggle. A mounting support plate is mounted inside the housing shell and operatively attaches thereto a power source and a printed circuit board (PCB) assembly, which are likewise disposed inside the housing shell. The power source includes a rechargeable battery that stores and selectively dispenses electrical power. The PCB assembly contains a system controller that connects to and controls the electrical input/output of the rechargeable battery. A pair of electrically conductive eyecups is movably attached to the mounting support plate and projects outward from a posterior side of the face goggle. The eyecups are electrically connected to the power source to receive therefrom an electrical microcurrent. Each eyecup is a single-piece, unitary structure with a pedestal and a pair of terminal rails, each of which projects from a respective edge of a longitudinal (posterior) end of the pedestal. Each pair of terminal rails physically contacts and thereby transmits the electrical microcurrent through a respective eyelid of the user.

Aspects of this disclosure are also directed to methods for manufacturing and methods for operating any of the herein described microcurrent systems and devices. In an example, a method is presented for manufacturing a quick-connect fluid coupler for fluidly coupling a fluid source to a fluid conduit. This representative method includes, in any order and in any combination with any of the above and below disclosed options and features: receiving a mounting support; receiving a power source configured to store and dispense electrical power; electrically connecting a system controller to the power source, the system controller being configured to control output of the electrical power by the power source; attaching a pair of eyecups to the mounting support; and electrically connecting the eyecups to the power source to receive therefrom the electrical power, the eyecups each including a pedestal with first and second terminal rails projecting from respective sides of a longitudinal end of the pedestal, the first and second terminal rails being configured to contact an eyelid of the user.

For any of the disclosed microcurrent systems, methods, and devices, each eyecup—including the pedestal and adjoining terminal rails—may be fabricated as a single-piece structure from an electrically conductive material. The electrically conductive material may include aluminum, copper, silver, gold, steel, silver-coated aluminum, gold-plated steel, metal-coated polymers, etc. As a further option, each terminal rail may include a curvilinear contact rail and a pair of arcuate connecting arms, each of which projects from a respective end of the curvilinear contact rail and connects to the pedestal. Each curvilinear contact rail is structurally configured (e.g., shaped, sized, and oriented) to press against a respective (upper or lower) eyelid flap of the user's eyelid. The pedestal may have an elongated right-circular cylinder shape; in this instance, the first (top) terminal rail may project longitudinally (rearward) from a first (top) edge of a longitudinal (rear) end of the pedestal, and the second (bottom) terminal rail may project longitudinally (rearward) from a second (bottom) edge, opposite the first edge, of the pedestal's longitudinal end. Each of the terminal rails may have an annular shape with a generally rectangular profile.

For any of the disclosed microcurrent systems, methods, and devices, a pair of skate plates may be attached to the mounting support; each skate plate movably mounts thereto a respective one of the eyecups. To provide such moveable engagement, each skate plate may be fabricated as a single-piece structure from a metallic material, and a respective magnet releasably and slidably mounts the eyecup to a respective ones of the skate plates. As a further option, an eyecup trolley may be slidably mounted to the mounting support. In this instance, each skate plate may be mounted to a respective side of the eyecup trolley such that the skate plates are thereby movably attached to the mounting support. A worm gear may be rotatably mounted to the mounting support and threadably mated, e.g., with helical threads or a dowel pin, of the eyecup trolley. In so doing, rotation of the worm gear causes the eyecup trolley to translate, e.g., in a reciprocating manner, along an antero-posterior rectilinear path. A pair of S-shaped mounting brackets may rigidly mount the skate plates to their respective sides of the eyecup trolley.

For any of the disclosed microcurrent systems, methods, and devices, a headgear component worn on the user's head may be employed to house the microcurrent system, e.g., for standalone headset applications. The headgear component may include an adjustable strap, cap, or similarly suitable structure for securing the headgear component to the user's head. The headgear component mounts thereto the mounting support, with the power source, system controller, and eyecups secured onto the mounting support. The headgear component may include a face goggle that abuts the face of the user, and a housing shell that is mounted to the face goggle. The face goggle may include a rigid polymeric frame, a fabric eye cover mounted to the polymeric frame and defining a rear surface of the goggle, and a face pad that presses against the user's face. In this instance, the mounting support, power source, and system controller are disposed inside the housing shell whereas the electrically conductive eyecups project outwards from the face goggle on a side thereof opposite the housing shell.

The above summary does not represent every embodiment or every aspect of the present disclosure. Rather, the foregoing summary merely provides a synopsis of some of the novel concepts and features set forth herein. The above features and advantages, and other features and attendant advantages of this disclosure, will be readily apparent from the following Detailed Description of illustrated examples and representative modes for carrying out the disclosure when taken in connection with the accompanying drawings and appended claims. Moreover, this disclosure expressly includes any and all combinations and subcombinations of the elements and features presented above and below.

Figure 1:
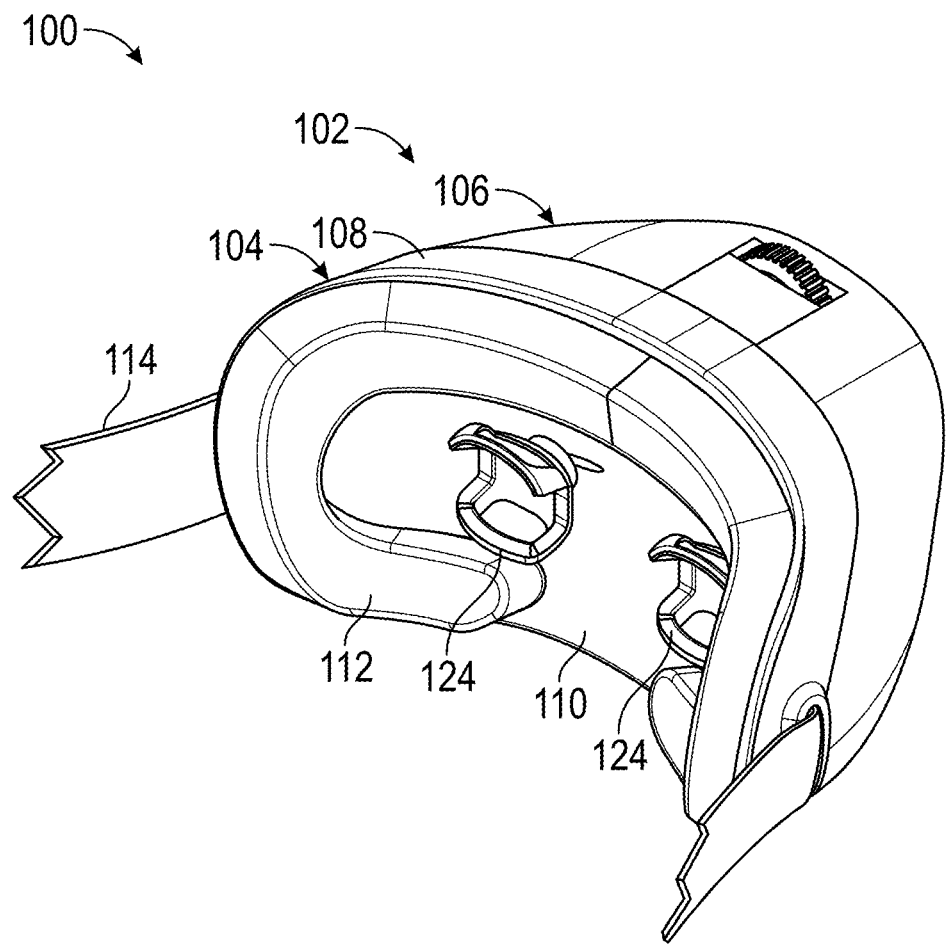
FIG. 1 is a rear, perspective-view illustration of a representative microcurrent headset device for treatment of a retinal disorder, visual impairment, or other ocular disease in accordance with aspects of the present disclosure.

The present disclosure is amenable to various modifications and alternative forms, and some representative embodiments of the disclosure are shown by way of example in the drawings and will be described in detail herein. It should be understood, however, that the novel aspects of this disclosure are not limited to the particular forms illustrated in the above-enumerated drawings. Rather, this disclosure covers all modifications, equivalents, combinations, permutations, groupings, and alternatives falling within the scope of this disclosure as encompassed, for example, by the appended claims.

DETAILED DESCRIPTION

This disclosure is susceptible of embodiment in many different forms. Representative embodiments of the disclosure are shown in the drawings and will herein be described in detail with the understanding that these embodiments are provided as an exemplification of the disclosed principles, not limitations of the broad aspects of the disclosure. To that extent, elements and limitations that are described, for example, in the Abstract, Technical Field, Introduction, Summary, Brief Description of the Drawings, and Detailed Description sections, but not explicitly set forth in the claims, should not be incorporated into the claims, singly or collectively, by implication, inference or otherwise. Moreover, recitation of "first", "second", "third", etc., in the specification or claims is not per se used to establish a serial or numerical limitation; unless specifically stated otherwise, these designations may be used for ease of reference to similar features in the specification and drawings and to demarcate between similar elements in the claims.

For purposes of this disclosure, unless explicitly disclaimed: the singular includes the plural and vice versa (e.g., indefinite articles "a" and "an" are to be construed as meaning "one or more"); the words "and" and "or" shall be both conjunctive and disjunctive; the words "any" and "all" shall both mean "any and all"; and the words "including," "containing," "comprising," "having," and the like, shall each mean "including without limitation." Moreover, words of approximation, such as "about," "almost," "substantially," "generally," "approximately," and the like, may each be used herein to denote "at, near, or nearly at," or "within 0-5% of," or "within acceptable manufacturing tolerances," or any logical combination thereof, for example.

Referring now to the drawings, wherein like reference numbers refer to like features throughout the several views, there is shown in FIG. 1 a perspective-view illustration of a representative therapeutic microcurrent system, which is designated generally at 100 and portrayed herein for purposes of discussion as a standalone microcurrent headset unit for treating age-related macular degeneration (AMD). The illustrated microcurrent headset unit 100—also referred to herein as "microcurrent system" or "microcurrent device"—is merely an exemplary application with which novel aspects of this disclosure may be practiced. In the same vein, implementation of the present concepts to treat AMD should also be appreciated as an exemplary application of the novel concepts disclosed herein. As such, it will be understood that features of this disclosure may be incorporated into other therapeutic microcurrent system architectures (e.g., countertop ophthalmic stand, freestanding kiosk, handheld therapy device, etc.) and utilized to treat any logically relevant type of visual impairment. Lastly, only select components of the therapeutic microcurrent system have been shown and will be described in additional detail herein. Nevertheless, the microcurrent systems and devices discussed below may include numerous additional and alternative features, and other available peripheral hardware for carrying out the various methods and functions of this disclosure.

Figure 2:
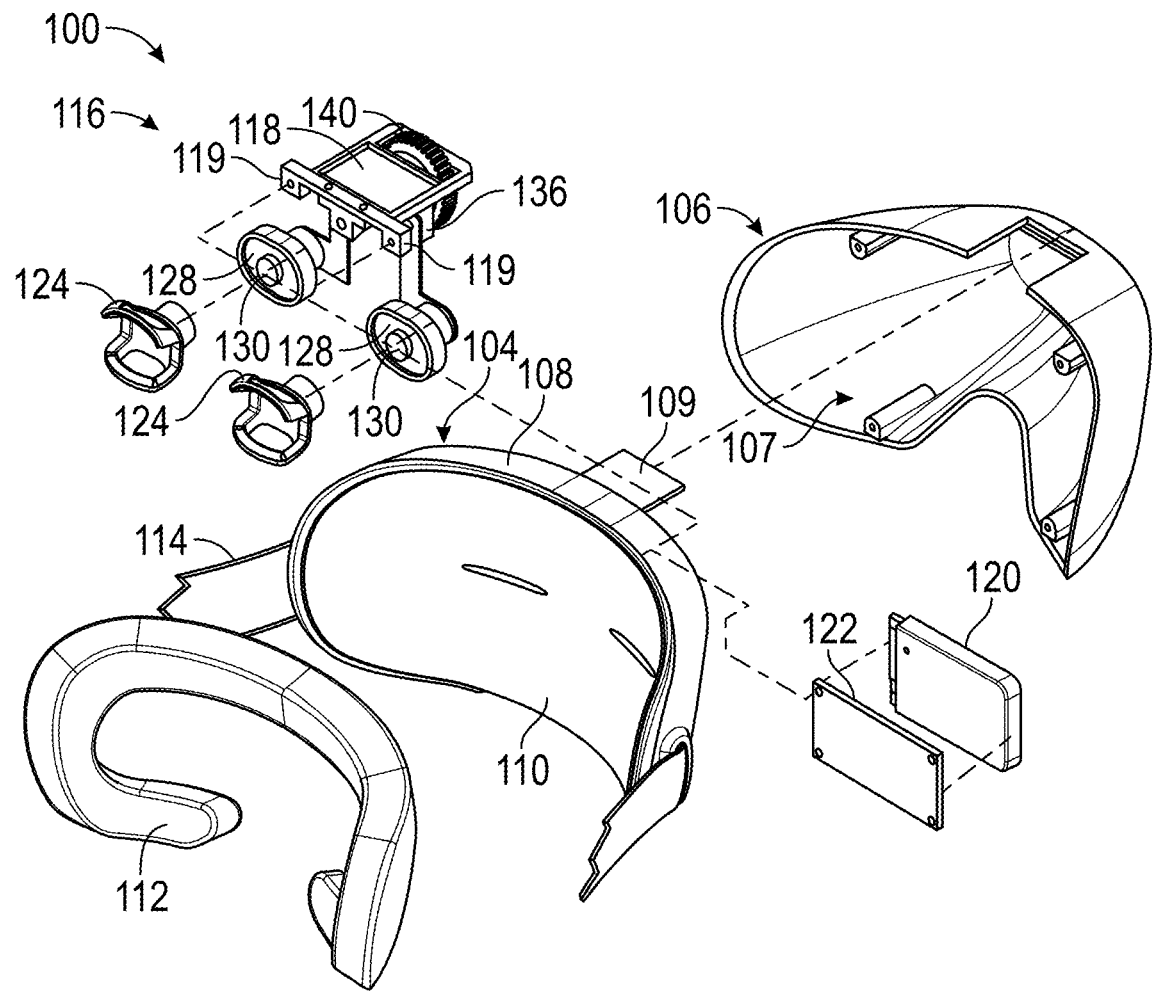
FIG. 2 is a partially exploded rear, perspective-view illustration of the representative microcurrent headset device of FIG. 1.

FIG. 1 illustrates an example of a manually operated, standalone electrotherapeutic headset that provides microcurrent stimulation therapy to treat patients suffering from macular degeneration and other visual impairments. In accord with the illustrated example, the microcurrent headset unit 100 includes a headgear component 102 that is designed to be worn on the head of a user. The headgear component 102 of FIG. 1 is generally composed of a face goggle 104 (or "eye mask") that abuts the user's face, and a housing shell 106 (or "front cone") that is mounted onto a first (anterior) side of the face goggle 104 to cooperatively define an interior compartment 107 (FIG. 2). The face goggle 104 may be a quadripartite assembly typified by a rigid and annular polymeric goggle frame 108, a flexible fabric eye cover 110, a compressible face pad 112, and an adjustable goggle strap 114. As shown, the fabric eye cover 110 is mounted to and stretches across the goggle frame 108 to define a rear surface of the goggle 104. The face pad 112 may be fastened or adhered to the exterior surface of the eye cover 110 and project rearward from the goggle frame 108 to press against the orbicularis oculi region of the user's face. The goggle strap 114 projects aftward from the face goggle 104 and wraps around the user's cranium to secure the headgear component 102 to their head.

It is envisioned that the face google 104 may employ an alternative fastening mechanism for securing the headgear component 102 to the user's head, such as an adjustable cap or a pair of eyeglass temple arms. Alternatively, the headgear component 102 may altogether omit a fastening mechanism, such as for handheld and countertop form factors. Depending on the intended application, the headgear component 102 may take on alternative shapes and sizes and, if desired, may include greater or fewer components than that which are shown in the drawings. For instance, the face goggle 104 and housing shell 106 may be formed as a one-piece structure, the face goggle 104 and eye cover 110 may be formed as a one-piece structure, the face pad 112 may be omitted, etc.

Figure 3:
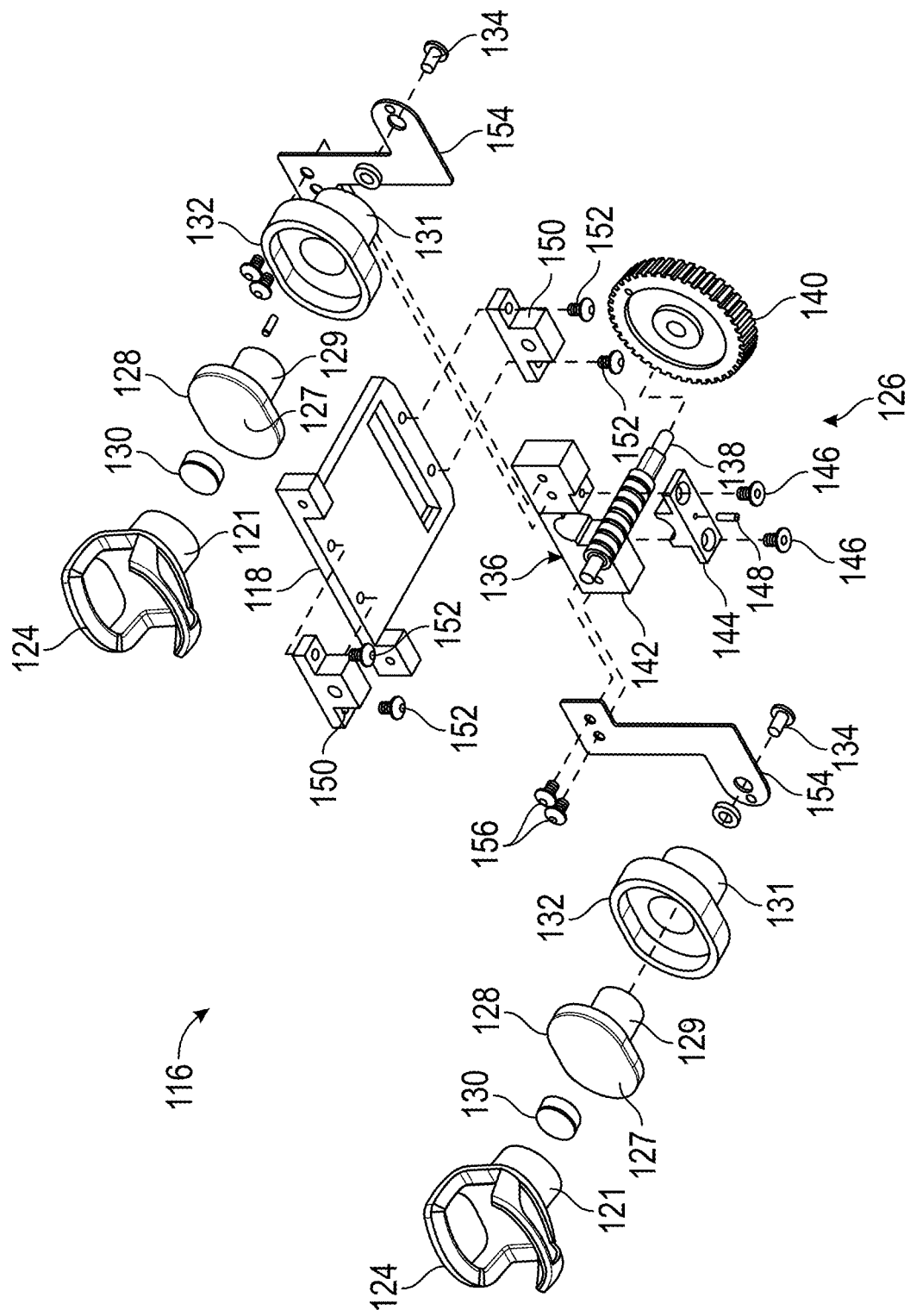
FIG. 3 is an exploded bottom, perspective-view illustration of the eyecup assembly of the representative microcurrent headset device of FIG. 1.

With reference next to FIG. 2, the housing shell 106 is secured to the face goggle 104, e.g., via four flat-head screws, to form a rigid outer housing for protecting the electronic and mechanical hardware of the microcurrent headset unit 100. The representative headset unit 100 presented in FIG. 2, for example, contains an eyecup assembly 116 with a mounting support plate 118 (or "mounting support"), a power source 120, a system controller 122, a pair of (left and right) electrically conductive eyecups 124, and an eyecup trolley subassembly 126 (FIG. 3). When the headset unit 100 is fully assembled, the mounting support plate 118, power source 120, system controller 122, and eyecup trolley subassembly 126 are disposed inside the housing shell 106. Conversely, the two eyecups 124 are located on the exterior of the face goggle 104, projecting rearwardly from the eye cover 110 portion (e.g., to the left in FIG. 1). This will allow the user to individually adjust both the vertical and lateral positioning of the eyecups 124 on the face goggle 104. The mounting support plate 118 may rigidly mount, e.g., via rivets, threaded fasteners, heat stakes, or sonic welding, to an underside surface of an integral mounting tab 109 that projects forward from the face goggle 104 (e.g., to the right in FIG. 1). It is also envisioned that the mounting support plate 118 may mount onto the housing shell 106 or, alternatively, may be integrally formed with the goggle 104 or the shell 106.

To provide structural support for the electronic and mechanical hardware of the microcurrent headset unit 100, the power source 120, system controller 122, eyecups 124, and trolley subassembly 126 may be securely mounted onto the mounting support plate 118. While illustrated and described as a substantially flat and rigid plate-like polymetric structure, the mounting support 118 may take on innumerable combinations of shapes, sizes, and materials to accommodate different design topologies. In a non-limiting example, the power source 120 is portrayed in FIG. 2 as a 3.7 volt (V), 2000 milliamp-hour (mAh) rechargeable lithium-ion battery pack that stores and selectively dispenses electrical power. The representative system controller 122 is portrayed as a single-sided, flexible control PCB assembly, e.g., with a resident microprocessor, an embedded RAM/ROM memory, an HMI interface, and an optional wireless short-range communication (SRC) device. Both the power source 120 and system controller 122 may physically mount, e.g., via panhead socket-type bolts, to complementary mounting flanges 119 projecting from a rear edge of the mounting support plate 118. The system controller 122 operatively connects, e.g., via dedicated battery dock, to the power source 120 to control the input/output of electrical power to/from the power source 120.

The headset unit 100 may also come equipped with an optional human-machine interface (HMI), such as an electromechanical pushbutton panel or an interactive touchscreen display, that provides the user with buttons, knobs, dials, indicators, and other input/output controls for operating the headset unit 100. For simplicity of design, the HMI may be a shell-mounted button and light panel with: (1) an ON/OFF button; (2) a MODE selection button (e.g., set microcurrent level, duty cycle, frequency, total duration, etc.); (3) a LOW BATTERY light indicator; (4) a system ON light indicator; and (5) LOW, MEDIUM, HIGH mode light indicators. It is envisioned that system control of the headset unit 100 may be offboarded, in whole or in part, to a dedicated software application operating on the user's personal computing device, which may be in the nature of a wireless or wired piggyback connection to a smartphone, laptop computer, or tablet computer.

Referring to both FIGS. 2 and 3, the eyecup assembly 116 incorporates a pair of electrically conductive (left and right) skate plates 128 that provide both a mounting interface and an electrical junction for the eyecups 124. For instance, first (posterior) ends of the skate plates 128 support thereon the eyecups 124, whereas second (anterior) ends of the skate plates 128 movably mount to an underside surface of the support plate 118, e.g., via the eyecup trolley subassembly 126 of FIG. 3. To accommodate users of differing facial topographies, each of the eyecups 124 may be slidably and removably mounted to a respective one of the skate plates 128 to thereby allow a user to selectively reposition the eyecups 124 with respect to the face goggle 104. The illustrated skate plates 128, for example, may be substantially structurally identical to each other with each skate plate 128 fabricated as a one-piece structure from a metallic material (e.g., precision machined steel). A button-shaped magnet 130 may be seated inside a complementary cavity 131 (FIG. 1) that is recessed into a terminal (posterior) end of each eyecup 124 and secured thereto, e.g., via an electrically conductive epoxy adhesive. When properly seated, these magnets 130 couple the eyecups 124 to rear faces of the skate plates 128.

Along with providing the aforementioned slidable and removable mounting interface, the skate plates 128 may also act as electrical terminals for electrically connecting the eyecups 124 to the power source 120. By way of non-limiting example, each skate plate 128 may have a T-shaped profile defined by a substantially flat rear faceplate 127 that is seated on and extends transversely across a first (posterior) end of a cylindrical base 129. Each of the skate plate bases 129 is sheathed inside a complementary sleeve 131 of an electrically insulating skate plate housing 132, which may be injection molded from acrylonitrile butadiene styrene (ABS) or thermoplastic nylon. The eyecups 124 electrically connect to the skate plates 128 by magnetically coupling the eyecups' elongated pedestals 121 onto the skate plates' rear faceplate 127. Each skate plate 128, in turn, is electrically connected to the control PCB assembly 122 and, thus, the rechargeable battery pack 120 via an electrical wire and mated wire terminal that is secured to a second (anterior) end of the skate plate base 129 via an electrical screw 134.

In addition to the skate plates 128 providing selective medio-lateral adjustment of the eyecups 124, the trolley subassembly 126 provides selective antero-posterior adjustment of the eyecups 124. As best seen in FIG. 3, for example, the trolley subassembly 126 may be composed of a bipartite eyecup trolley 136, a cylindrical worm gear 138, and a beveled worm wheel 140. The eyecup trolley 136 includes a trolley block 142 that slides along the underside surface of the mounting support plate 118, and a trolley rack 144 that mounts to the underside of the trolley block 142, e.g., via threaded bolts 146. When assembled, the eyecup trolley 136 receives therethrough and rides on the worm gear 138 such that the external teeth of the worm gear 138 threadably mates with a dowel pin 148 or internally projecting threads of the trolley rack 144. Unthreaded terminal ends of the worm gear 138 are rotatably inserted into complementary through-holes in mounting blocks 150, which are located at opposite ends of the worm gear 138 and mount to the underside of the support plate 118, e.g., via four threaded bolts 152.

Each skate plate 128, including the skate plate housing 132 and eyecup 124 secured thereto, mounts to a respective side of the eyecup trolley 136 such that fore-aft movement of the trolley 136 engenders fore-aft movement of the eyecups 124. By way of example, and not limitation, a pair of substantially flat and rigid S-shaped mounting brackets 154 rigidly mounts the skate plates 127 to their respective sides of the eyecup trolley 136, e.g., via threaded bolts 156. The beveled worm wheel 140 is keyed or splined to one of the unthreaded terminal ends of the worm gear 138 such that manual rotation of the worm wheel 140 causes rotation of the worm gear 138. Rotation of the worm gear 138, through its threaded engagement with the trolley rack 144, causes the eyecup trolley 136 to translate, e.g., in a reciprocating manner, along an antero-posterior rectilinear path (e.g., left and right in FIG. 3).

The electrically conductive eyecups 124 act as working electrodes that are designed to simultaneously contact the palpebra cutanea of the upper and lower eyelid flaps of both of the user's eyes to transmit therethrough a therapeutic microcurrent, e.g., of about 20 to about 500 microamps (µA). For simplicity of design and manufacture, it may be desirable that the two eyecups 124 be substantially structurally identical to each other. As best seen in FIGS. 4A-4D, for example, each of the eyecups 124 includes an elongated and rigid pedestal 121 with a pair of arched (top and bottom) terminal rails 123 and 125 that each projects from a respective (top or bottom) side of a longitudinal (posterior) end of the pedestal 121. Each eyecup 124—including the pedestal 121 and adjoining terminal rails 123, 125—may be fabricated as a one-piece, unitary structure from an electrically conductive material. The electrically conductive material may include, in some non-limiting examples, aluminum, copper, silver, gold, steel, silver-coated aluminum, gold-plated steel, metal-coated polymers, etc. For at least some applications, the eyecups 124 are either machined aluminum substratum that are plated or coated in silver, or 3D-printed stainless steel substratum that are plated or coated in gold. The pedestal 121 may have an elongated right-circular cylinder shape; in this instance, the first (top) terminal rail 123 may project longitudinally (rearward) at an oblique angle (e.g., approximately) 15-25° from a first (top) edge of a longitudinal (rear) end of the pedestal 121, whereas the second (bottom) terminal rail 125 may project longitudinally (rearward) at an oblique angle from a second (bottom) edge, opposite the first edge, of the pedestal's longitudinal end.

Figure 4B:
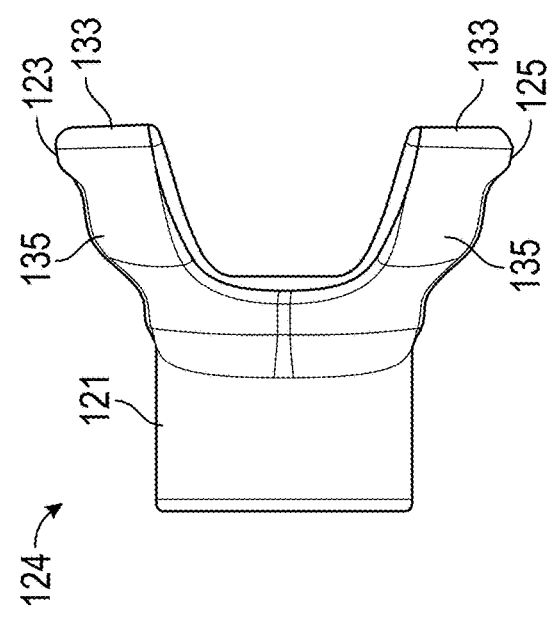
FIGS. 4A-4D are end-view (FIG. 4A), side-view (FIG. 4B), plan-view (FIG. 4C), and sectional side-view (FIG. 4D) illustrations of one of the electrically conductive eyecups of the representative microcurrent headset device of FIG. 1.
Figure 4D:
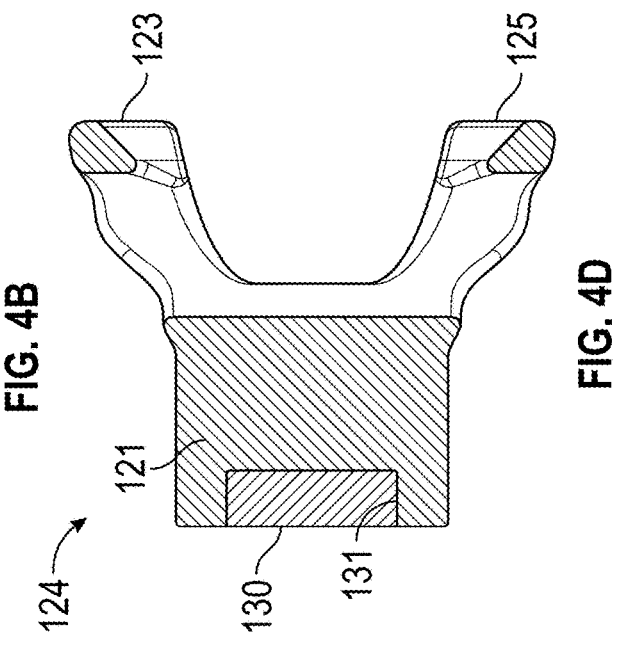
Figure 4A:
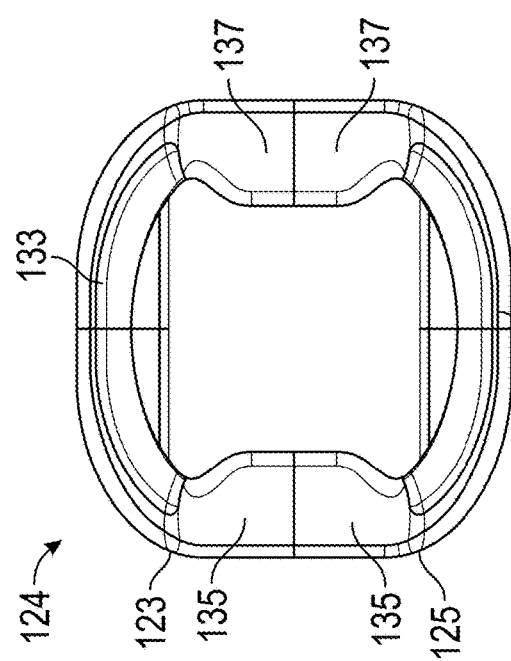
Figure 4C:
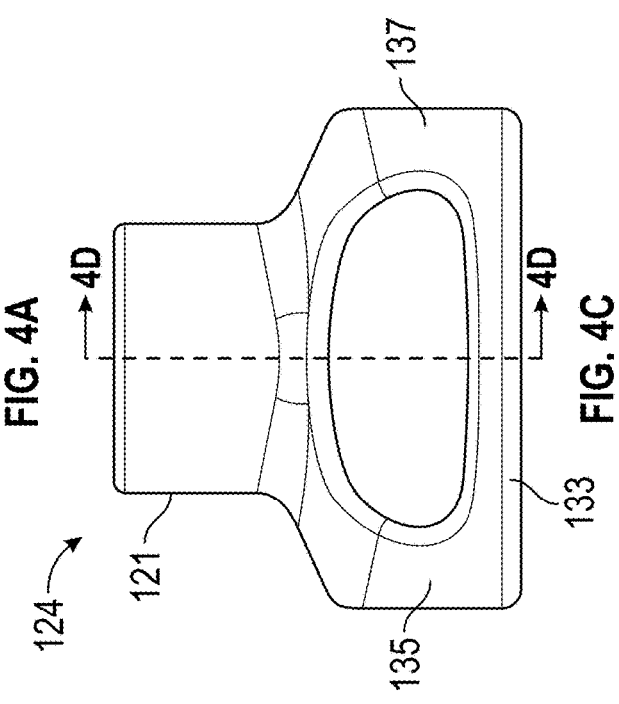

Each terminal rail 123, 125 of each eyecup 124 is structurally configured (e.g., shaped, sized, and oriented) to contact a respective eyelid flap of the user, e.g., to transmit an electrical microcurrent through the eyelid to the user's eyes. With continuing reference to FIGS. 4A-4D, each terminal rail 123, 125 may be fabricated with a curvilinear contact rail 133 that extends in a mediolateral direction with respect to the user's face and eyes. The first (upper) contact rail 133 is shown in FIG. 4A with a semi-ellipsoidal, concave-down orientation, whereas the second (lower) contact rail 133 is shown with a semi-ellipsoidal, concave-up orientation. A pair of arcuate (left and right) connecting arms 135 and 137 each projects from a respective lateral end of the curvilinear contact rail 133 and joins to the longitudinal (posterior) end of the pedestal 121, as best seen in FIGS. 4B and 4C. With this configuration, each curvilinear contact rail 133 will press against a respective eyelid flap of an eyelid of the user and sit substantially flush against that flap. As best seen with collective reference to both FIGS. 4A and 4C, each terminal rail 123, 125 may have a ring-like "annular" shape with a generally rectangular outer profile. During operation of the microcurrent headset unit 100, each eyecup 124 may act as both a positive (cathode) electrode and negative (anode) electrode, such that when the left eyecup 124 is positive the right eyecup 124 is negative and when the left eyecup 124 is negative the right eyecup 124 is positive. Alternative system configurations may drive both eyecups 124 as positive electrodes and use a metallic fabric eye cover as a negative "return" electrode.

Aspects of the present disclosure have been described in detail with reference to the illustrated embodiments; those skilled in the art will recognize, however, that many modifications may be made thereto without departing from the scope of the present disclosure. The present disclosure is not limited to the precise construction and compositions disclosed herein; any and all modifications, changes, and variations apparent from the foregoing descriptions are within the scope of the disclosure as defined by the appended claims. Moreover, the present concepts expressly include any and all combinations and subcombinations of the preceding elements and features.

Additional features may be reflected in the following clauses:

Clause 1: a microcurrent system for treating an ocular disease of a user, the microcurrent system comprising: a mounting support; a power source configured to store and dispense electrical power; a system controller electrically connected to the power source and configured to control output of the electrical power by the power source; and a pair of eyecups attached to the mounting support and electrically connected to the power source to receive therefrom the electrical power, the eyecups each including a pedestal with first and second terminal rails projecting from respective sides of a longitudinal end of the pedestal, the first and second terminal rails being configured to contact an eyelid of the user.

Clause 2: the microcurrent system of clause 1, wherein each of the eyecups, including the pedestal and the first and second terminal rails, is fabricated as a single-piece structure from an electrically conductive material.

Clause 3: the microcurrent system of clause 2, wherein the electrically conductive material includes aluminum, copper, silver, gold, and/or steel.

Clause 4: the microcurrent system of any one of clauses 1 to 3, wherein each of the first and second terminal rails includes a curvilinear contact rail with a pair of arcuate connecting arms projecting from respective ends of the curvilinear contact rail and joined to the pedestal, each of the curvilinear contact rails being configured to press against a respective eyelid flap of the eyelid of the user.

Clause 5: the microcurrent system of clause 4, wherein the pedestal has an elongated cylindrical shape, and wherein the first terminal rail projects longitudinally from a first edge of the longitudinal end of the pedestal, and the second terminal rail projects longitudinally from a second edge, opposite the first edge, of the longitudinal end of the pedestal.

Clause 6: the microcurrent system of clause 4, wherein each of the first and second terminal rails has an annular shape with a generally rectangular profile.

Clause 7: the microcurrent system of any one of clauses 1 to 6, further comprising a pair of skate plates attached to the mounting support and each movably mounting thereto a respective one of the eyecups.

Clause 8: the microcurrent system of clause 7, wherein each of the skate plates is fabricated as a single-piece structure from a metallic material, the microcurrent system further including a pair of magnets releasably mounting the eyecups to respective ones of the skate plates.

Clause 9: the microcurrent system of clause 7, further comprising an eyecup trolley slidably mounted to the mounting support, each of the skate plates mounted to a respective side of the eyecup trolley and thereby movably attached to the mounting support.

Clause 10: the microcurrent system of clause 9, further comprising a worm gear rotatably mounted to the mounting support and threadably mated with the eyecup trolley such that rotation of the worm gear causes the eyecup trolley to translate along a rectilinear path.

Clause 11: the microcurrent system of clause 10, further comprising a pair of S-shaped mounting brackets each rigidly mounting a respective one of the skate plates to the respective side of the eyecup trolley.

Clause 12: the microcurrent system of any one of clauses 1 to 11, further comprising a headgear component configured to be worn on the head of the user, the headgear component mounting thereto the mounting support with the power source, the system controller, and the pair of eyecups mounted onto the mounting support.

Clause 13: the microcurrent system of clause 12, wherein the headgear component includes a face goggle configured to abut the face of the user and a housing shell mounted to the face goggle, wherein the mounting support, the power source, and the system controller are disposed inside the housing shell and the pair of eyecups project outwards from the face goggle.

Clause 14: a microcurrent headset unit for treating an ocular disease of a user with a head and a face, the microcurrent headset unit comprising: a headgear component configured to be worn on the head of the user, the headgear component including a face goggle configured to abut the face of the user and a housing shell mounted to the face goggle; a mounting support plate mounted inside the housing shell; a power source including a rechargeable battery disposed inside the housing shell, attached to the mounting support plate, and configured to store and dispense electrical power; a printed circuit board (PCB) assembly with a system controller disposed inside the housing shell, attached to the mounting support plate, and electrically connected to the power source to control output of the electrical power by the rechargeable battery; and a pair of eyecups movably attached to the mounting support plate, projecting outwards from the face goggle, and electrically connected to the power source to receive therefrom an electrical microcurrent, the eyecups each fabricated as a single-piece structure from an electrically conductive material and including a pedestal with first and second terminal rails each projecting from a respective edge of a longitudinal end of the pedestal, the first and second terminal rails configured to contact and thereby transmit the electrical microcurrent to an eyelid of the user.

Clause 15: a method of assembling a microcurrent system for treating an ocular disease of a user, the method comprising: receiving a mounting support; receiving a power source configured to store and dispense electrical power; electrically connecting a system controller to the power source, the system controller being configured to control output of the electrical power by the power source; attaching a pair of eyecups to the mounting support; and electrically connecting the eyecups to the power source to receive therefrom the electrical power, the eyecups each including a pedestal with first and second terminal rails projecting from respective sides of a longitudinal end of the pedestal, the first and second terminal rails being configured to contact an eyelid of the user.

Clause 16: the method of clause 15, wherein each of the eyecups, including the pedestal and the first and second terminal rails, is fabricated as a single-piece structure from an electrically conductive material.

Clause 17: the method of clause 16, wherein the electrically conductive material includes aluminum, copper, silver, gold, and/or steel.

Clause 18: the method of any one of clauses 15 to 17, wherein each of the first and second terminal rails includes a curvilinear contact rail with a pair of arcuate connecting arms projecting from respective ends of the curvilinear contact rail and joined to the pedestal, each of the curvilinear contact rails being configured to press against a respective eyelid flap of the eyelid of the user.

Clause 19: the method of clause 18, wherein the pedestal has an elongated cylindrical shape, and wherein the first terminal rail projects longitudinally from a first edge of the longitudinal end of the pedestal, and the second terminal rail projects longitudinally from a second edge, opposite the first edge, of the longitudinal end of the pedestal.

Clause 20: the method of clause 18, wherein each of the first and second terminal rails has an annular shape with a generally rectangular profile.

Clause 21: the method of any one of clauses 15 to 20, further comprising attaching a pair of skate plates to the mounting support, each of the skate plates movably mounting thereto a respective one of the eyecups.

Clause 22: the method of clause 21, wherein each of the skate plates is fabricated as a single-piece structure from a metallic material, the method further comprising releasably mounting each of the eyecups to a respective one of the skate plate via a respective magnet.

Clause 23: the method of clause 21, further comprising slidably mounting an eyecup trolley to the mounting support, wherein each of the skate plates is mounted to a respective side of the eyecup trolley and thereby movably attached to the mounting support.

Clause 24: the method of clause 23, further comprising: rotatably mounting a worm gear to the mounting support; and threadably mating the worm gear with the eyecup trolley such that rotation of the worm gear causes the eyecup trolley to translate along a rectilinear path.

Clause 25: the method of clause 24, further comprising: mounting each of the skate plates to a respective S-shaped mounting bracket; and mounting each of the S-shaped mounting brackets to the respective side of the eyecup trolley.

Clause 26: the method of any one of clauses 15 to 25, further comprising: receiving a headgear component configured to be worn on the head of the user; mounting the power source, the system controller, and the pair of eyecups onto the mounting support; and mounting the mounting support to the headgear component.

Clause 27: the method of clause 26, wherein the headgear component includes a face goggle configured to abut the face of the user and a housing shell mounted to the face goggle, wherein the mounting support, the power source, and the system controller are disposed inside the housing shell and the pair of eyecups project outwards from the face goggle.

What is claimed:

1. A microcurrent system for treating an ocular disease of a user, the microcurrent system comprising:
a mounting support;
a power source configured to store and dispense electrical power;
a system controller electrically connected to the power source and configured to control output of the electrical power by the power source;
a pair of eyecups electrically connected to the power source to receive therefrom the electrical power, the eyecups each including a pedestal with first and second terminal rails projecting from respective sides of a longitudinal end of the pedestal, the first and second terminal rails being configured to contact an eyelid of the user;
a pair of skate plates each mounting thereto a respective one of the eyecups; and
an eyecup trolley slidably mounted to the mounting support, each of the skate plates mounted to a respective side of the eyecup trolley and thereby movably attached to the mounting support.

2. The microcurrent system of claim 1, wherein each of the eyecups, including the pedestal and the first and second terminal rails, is fabricated as a single-piece structure from an electrically conductive material.

3. The microcurrent system of claim 2, wherein the electrically conductive material includes aluminum, copper, silver, gold, and/or steel.

4. The microcurrent system of claim 1, wherein each of the first and second terminal rails includes a curvilinear contact rail with a pair of arcuate connecting arms projecting from respective ends of the curvilinear contact rail and joined to the pedestal, each of the curvilinear contact rails being configured to press against a respective eyelid flap of the eyelid of the user.

5. The microcurrent system of claim 4, wherein the pedestal has an elongated cylindrical shape, and wherein the first terminal rail projects longitudinally from a first edge of the longitudinal end of the pedestal, and the second terminal rail projects longitudinally from a second edge, opposite the first edge, of the longitudinal end of the pedestal.

6. The microcurrent system of claim 4, wherein each of the first and second terminal rails has an annular shape with a generally rectangular profile.

7. The microcurrent system of claim 1, wherein each of the skate plates movably mounts thereto the respective one of the eyecups.

8. The microcurrent system of claim 1, wherein each of the skate plates is fabricated as a single-piece structure from a metallic material, the microcurrent system further including a pair of magnets releasably mounting the eyecups to respective ones of the skate plates.

9. The microcurrent system of claim 1, further comprising a worm gear rotatably mounted to the mounting support and threadably mated with the eyecup trolley such that rotation of the worm gear causes the eyecup trolley to translate along a rectilinear path.

10. The microcurrent system of claim 9, further comprising a pair of S-shaped mounting brackets each rigidly mounting a respective one of the skate plates to the respective side of the eyecup trolley.

11. The microcurrent system of claim 1, further comprising a headgear component configured to be worn on the head of the user, the headgear component mounting thereto the mounting support with the power source, the system controller, the skate plates, the eyecup trolley, and the pair of eyecups mounted onto the mounting support.

12. The microcurrent system of claim 11, wherein the headgear component includes a face goggle configured to abut the face of the user and a housing shell mounted to the face goggle, wherein the mounting support, the power source, and the system controller are disposed inside the housing shell and the pair of eyecups project outwards from the face goggle.

13. A microcurrent headset unit for treating an ocular disease of a user with a head and a face, the microcurrent headset unit comprising:
 a headgear component configured to be worn on the head of the user, the headgear component including a face goggle configured to abut the face of the user and a housing shell mounted to the face goggle,
 a mounting support plate mounted inside the housing shell,
 a power source including a rechargeable battery disposed inside the housing shell, attached to the mounting support plate, and configured to store and dispense electrical power,
 a printed circuit board (PCB) assembly with a system controller disposed inside the housing shell, attached to the mounting support plate, and electrically connected to the power source to control output of the electrical power by the rechargeable battery,
 a pair of eyecups projecting outwards from the face goggle and electrically connected to the power source to receive therefrom an electrical microcurrent, the eyecups each fabricated as a single-piece structure from an electrically conductive material and including a pedestal with first and second terminal rails each projecting from a respective edge of a longitudinal end of the pedestal, the first and second terminal rails configured to contact and thereby transmit the electrical microcurrent to an eyelid of the user,
 a pair of skate plates each mounting thereto a respective one of the eyecups; and
 an eyecup trolley slidablu mounted to the mounting support plate, each of the skate plates mounted to a respective side of the eyecup trolley and thereby movably attached to the mounting support.

14. A method of assembling a microcurrent system for treating an ocular disease of a user, the method comprising:
 receiving a mounting support;
 receiving a power source configured to store and dispense electrical power;
 electrically connecting a system controller to the power source, the system controller being configured to control output of the electrical power by the power source;
 electrically connecting a pair of eyecups to the power source to receive therefrom the electrical power, the eyecups each including a pedestal with first and second terminal rails projecting from respective sides of a longitudinal end of the pedestal, the first and second terminal rails being configured to contact an eyelid of the user;
 mounting each of the eyecups to a respective one of a pair of skate plates;
 slidably mounting an eyecup trolley to the mounting support; and
 mounting each of the skate plates to a respective side of the eyecup trolley and thereby movably attaching the skate plates and the eyecups to the mounting support.

15. The method of claim 14, wherein each of the eyecups, including the pedestal and the first and second terminal rails, is fabricated as a single-piece structure from an electrically conductive material.

16. The method of claim 15, wherein the electrically conductive material includes aluminum, copper, silver, gold, and/or steel.

17. The method of claim 14, wherein each of the first and second terminal rails includes a curvilinear contact rail with a pair of arcuate connecting arms projecting from respective ends of the curvilinear contact rail and joined to the pedestal, each of the curvilinear contact rails being configured to press against a respective eyelid flap of the eyelid of the user.

18. The method of claim 17, wherein the pedestal has an elongated cylindrical shape, and wherein the first terminal rail projects longitudinally from a first edge of the longitudinal end of the pedestal, and the second terminal rail projects longitudinally from a second edge, opposite the first edge, of the longitudinal end of the pedestal.

19. The method of claim 17, wherein each of the first and second terminal rails has an annular shape with a generally rectangular profile.

20. The method of claim 14, wherein each of the skate plates is fabricated as a single-piece structure from a metallic material, and wherein each of the eyecups includes a respective magnet releasably and slidably mounting the eyecup to the respective one of the skate plates.

* * * * *